US008187870B2

(12) United States Patent
Lemesre et al.

(10) Patent No.: US 8,187,870 B2
(45) Date of Patent: May 29, 2012

(54) **MEANS FOR OBTAINING AVIRULENT *LEISHMANIA* PROMASTIGOTES, PROMASTIGOTES OBTAINED, AND THE APPLICATIONS THEREOF**

(75) Inventors: Jean-Loup Lemesre, Montpellier (FR); Philippe Holzmuller, Poussan (FR); Rachel Bras-Gonçalves, Montpellier (FR)

(73) Assignee: Institut de Recherche pour le Developpement (IRD), Marseilles (FR)

( * ) Notice: Subject to any disclaimer, the term of this patent is extended or adjusted under 35 U.S.C. 154(b) by 229 days.

(21) Appl. No.: 11/884,015

(22) PCT Filed: Feb. 10, 2006

(86) PCT No.: PCT/FR2006/000314
§ 371 (c)(1), (2), (4) Date: Feb. 4, 2008

(87) PCT Pub. No.: WO2006/085011
PCT Pub. Date: Aug. 17, 2006

(65) Prior Publication Data
US 2009/0214595 A1 Aug. 27, 2009

(30) Foreign Application Priority Data
Feb. 10, 2005 (FR) ........................................ 0501348

(51) Int. Cl.
*C12N 1/20* (2006.01)
*C12N 15/00* (2006.01)
(52) U.S. Cl. ................................... 435/320.1; 435/252.3
(58) Field of Classification Search ........................ None
See application file for complete search history.

(56) References Cited

U.S. PATENT DOCUMENTS

| 2002/0169285 A1 | 11/2002 | Reed et al. | |
|---|---|---|---|
| 2003/0068690 A1 | 4/2003 | Lemesre | |
| 2003/0157125 A1 | 8/2003 | Alvarez et al. | |
| 2008/0026467 A1* | 1/2008 | Lemesre et al. | 435/476 |

FOREIGN PATENT DOCUMENTS

WO 94/26899 11/1994

OTHER PUBLICATIONS

Shreffler et al (Journal of Infectious Diseases, vol. 167, No. 2, pp. 426-430, 1993).*
International Search Report for PCT/FR2006/000314 mailed Jun. 21, 2006 (English and French).
Chen et al., "Episomal Expression of Specific Sense and Antisense MRNAs in Leishmania Amazonensis: Modulation of GP63 Level in Promatigotes and their Infection of Macrophages in Vitro," Infection and Immunity, vol. 68, No. 1, 2000, 1980 p. 86, XP009051114.

Hajmova et al., "Down Regulation of GP63 in Leishmania Amazonensis Reduces its Early Development in Lutzomyia Longialpis," Microbes and Infection, vol. 6, 2004, pp. 646-649, XP009051117.
Joshi et al., "Targeted Gene Deletion in Leishmania Major Identifies Leishmanolysin (GP63) as a Virulence Factor," Molecular and Biochemical Parasitology, vol. 120, 2002, pp. 33-40, XP009051113.
Beverley et al., "Flypaper for Parasites," Cell, vol. 119, Oct. 29, 2004, pp. 311-316, XP009051110.
International Search Report for PCT/FR04/02955 dated Aug. 17, 2005.
Loman et al., *Molecular cloning and characterization of the immunologically protective surface glycoprotein GP46/M-2 of Leishmania amazonensis*, Proceedings of the National Academy of Sciences of USA, vol. 87, Nov. 1990, pp. 8393-8397, XP002204079.
Dumonteil et al., *DNA vaccines induce partial protection against Leishmania mexicana*, Vaccine, vol. 21, No. 17-18, May 16, 2003, pp. 2170-2177, XP004421134.
Handman et al., *Therapy of murine cutaneous leishmaniasis by DNA vaccination*, Vaccine, vol. 18, No. 26, Jul. 2000, pp. 3011-3017, XP004199096.
Lebowitz et al., *Development of a Stable Leishmania Expression Vector and Application to the Study of Parasite Surface Antigen Genes*, Proceedings of the National Academy of Science, vol. 87, Dec. 1990, pp. 9736-9740, XP002052133.
Kima et al., *Presentation via the class I pathway by Leishmania amazonensis-infected macrophages of an endogenous leishmanial antigen to CD8+ T cells*, Journal of Immunology, Aug. 15, 1997, vol. 159, No. 4, pp. 1828-1834, XP002336360.
Jimenez-Ruiz et al., *Cloning Sequencing and Expression of the PSA Genes from Leishmania infantum*, European Journal of Biochemistry, vol. 251, No. 1 / 2, Jan. 15, 1998, pp. 389-397, XP001159173.
Murray et al., *Variants of a Leishmania Surface Antigen Derived from a Multigenic Family*, Journal of Biological Chemistry, vol. 266, No. 36, 1991, pp. 24477-24484, XP002296789.
Symons et al., *Characterization of a polymorphic family of integral membrane proteins in promastigotes of different Leishmania species*, Molecular and Biochemical Parasitology, vol. 67, No. 1, 1994, pp. 103-113, XP002336361.
Beetham et al., *Glycoprotein 46 mRNA abundance is post-transcriptionally regulated during development of Leishmania chagasi promastigotes to an infectious form*, Journal of Biological Chemistry, vol. 272, No. 28, 1997, pp. 17360-17366, XP002296788.
Breitlow, "Selection of protein stains for SDS gel electrophoresis", Promega Notes Magazine No. 35, Feb. 1992.

* cited by examiner

*Primary Examiner* — Albert Navarro
(74) *Attorney, Agent, or Firm* — Nixon & Vanderhye P.C.

(57) ABSTRACT

The invention relates to an expression vector of a gene coding for an antigenic protein of *Leishmania* promastigote, characterized in that it comprises a PSA gene insert in opposite orientation. The invention can be applied to the development of mutants under-expressing, or no longer expressing, genes coding for an antigenic protein of *Leishmania* promastigote, and to the therapeutic and/or vaccine-oriented uses thereof.

6 Claims, 2 Drawing Sheets

Figure 1:
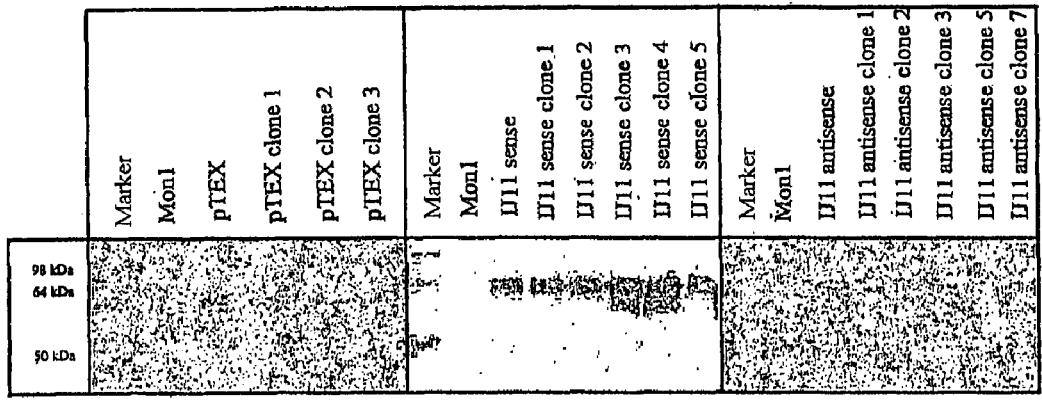

MEANS FOR OBTAINING AVIRULENT *LEISHMANIA* PROMASTIGOTES, PROMASTIGOTES OBTAINED, AND THE APPLICATIONS THEREOF

This application is the US national phase of international application PCT/FR2006/000314 filed 10 Feb. 2006, which designated the U.S. and claims benefit of FR 0501348, filed 10 Feb. 2005, the entire contents of each of which are hereby incorporated by reference.

The invention relates to means for obtaining avirulent *leishmania* promastigotes. It also relates to the promastigotes obtained and to the uses thereof, in particular in immunoprophylaxis.

*Leishmaniases* constitute worldwide endemic parasitic infections which represent a considerable public health problem affecting both developing countries and countries such as those of southern Europe, where they are considered to be opportunistic diseases in immuno-depressed individuals.

At the current time, no effective immunoprophylactic or immunotherapeutic means exist against *leishmaniases*, and more particularly against the responsible infectious agent, namely *leishmania* parasites.

*Leishmania* parasites are flagellate protozoa belonging to the Trypanosomatidae family and to the *Leishmania* genus. This family includes parasites which can infect humans, and certain animals such as rodents, canines, or mammals.

The biological cycle of protozoa of the *Leishmania* genus is shared between an invertebrate vector host, the sandfly (small hematophagous dipterous insect), and many vertebrates, including humans. The *leishmania* have a heteroxenous parasitic developmental cycle during which two distinct morphological stages follow on from one another. In the sandfly, the parasite is in a mobile, extracellular, flagellate form inside the digestive tube of the insect, called promastigote stage. In the invertebrate host, the parasite transforms into an immobile ovoid form of from 2 to 6 μm in diameter, with a very short flagellar residue, called amastigote, which will reside in the parasitophorous vacuole, in the cells of the reticulohistiocytic system, mainly macrophages.

The female hematophagous vector insect becomes infected via the blood of the contaminated vertebrate host, by ingestion of parasitized macrophages. Most of the ingested amastigotes are then destroyed in the following hours. The survivors transform into promastigotes, which will colonize the median intestine, where they actively multiply. They subsequently migrate to the anterior and buccal parts of the digestive tract and then undergo differentiation leading to the formation of metacyclic promastigotes which are highly infectious for the vertebrate host.

The vertebrate host is contaminated with the metacyclic promastigotes when it is bitten by an infected female sandfly. These promastigote forms are injected into the dermis together with saliva, and will then be phagocytized by the cells of the reticulohystiocytic system, in particular macrophages, inside which they differentiate into immobile intracellular amastigote forms. They will then actively multiply by schizogenesis inside the parasitophorous vacuole (phagolysosome) until lysis of the host cell is brought about, thus allowing the released amastigotes to propagate the infection by colonizing other normal macrophages. A further bite by a sandfly will result in infection of the latter and will allow the parasite to perpetuate its cycle.

Despite the advances in this field, *leishmaniases* still remain today a serious public health problem due to the number of individuals involved, the extent of the geographic area covered by the disease, and the diversity and seriousness of the clinical pictures observed.

The need for effective vaccines against *leishmaniases* and for novel therapeutic and/or vaccine-related targets for treating these parasitic diseases can therefore be seen.

During infection, the infectious promastigote forms injected into the mammalian host must evade the host's immune response in order to be able to subsequently invade the macrophages. The parasite must therefore implement mechanisms which allow it to escape this immune response and to be capable of adapting to a new environment. Early recognition of the parasite by the host organism during invasion may thus be a key step in resistance to the infection.

Surface antigens, lipophosphoglycan (LPG) and gp63 (metalloprotease), also called leishmanolysin, were discovered in the 1980s.

LPG is the major surface molecule of the promastigote forms, the role of which as a virulence factor has been confirmed.

gp63 is a major surface protease, also considered to be a virulence factor.

Antigens of a third type, called PSAs for "Promastigote Surface Antigens", were discovered in 1988-1989. They constitute the major surface antigens of the promastigote forms.

Excretory/secretory antigens (ESAs), which have been very widely studied in many parasitic microorganisms (nematodes, protozoa, etc.), play an important role in the infection and defense mechanisms of these parasites, since they have the possibility of acting remotely. In *leishmania*, research studies have for a long time been limited by the difficulty in being able to have ESAs available in sufficient amounts to study them.

All these antigens appear to play a determining role in the survival and infectiousness of the promastigote forms.

Prior studies by the inventor in this field had led to the development of completely defined culture media, without macromolecules and free of fetal calf serum, allowing the continuous culture of the promastigote and amastigote forms under axenic and serum-free conditions. These media, described in particular in patent application FR No. 93 05 779, have made it possible to reproduce, in vitro, the complete parasitic developmental cycle of *leishmania*, such as *L. amazonensis* and *L. infantum*, and to have, under natural conditions, a relatively abundant source of ESAs available by simply concentrating the culture medium supernatant metabolized by the parasites. A characterization of *leishmania* ESAs could thus be carried out.

Studies performed in the inventors, laboratory have thus shown that the major immunogen of the *L. amazonensis* ESAs has a molecular mass of 45 kDa. The screening of a promastigote-form cDNA expression library with a monoclonal antibody called E2, produced against this major immunogen, has made it possible to isolate and identify cDNA clones encoding proteins of the PSA family. This antibody is produced by the murine hybridoma IV D6/E2 deposited with the C.N.C.M, 28 rue du Dr Roux, Paris, France, on Nov. 10, 2004, under the No. I-3318, more especially by the murine hybridoma deposited on Feb. 3, 2006, with the CNCM under the No. I-3570. Thus, for the first time, three new PSA cDNA sequences expressed in the promastigote form of *L. amazonensis* were identified. These isolated cDNAs differ from one another by virtue of the number of LRRs (4, 6 or 7). More recently, a screening of an *L. infantum* promastigote cosmid library has been carried out using, as radiolabeled probe, the DNA encoding *L. amazonensis* PSA. A new *Leishmania* gene, IJ11, has been identified, encoding an excreted/secreted protein of L. infantum, of molecular mass 56 kDa (LiPSA 50s), belonging to the PSA family.

A functional study of the genes encoding PSAs, major immunogens of the excretory/secretory products of *leishmania*, was therefore undertaken using the tools provided by genomics. The experimental approach consisted in introducing, into the promastigotes of a *leishmania*, plasmid constructs capable of inducing a decrease in the level of production of the PSA in order to study the repercussions of these changes on the biology of the parasite and its virulence.

It thus appeared that the nondirectional cloning, in an expression vector for the IJ11 gene encoding the LiPSA 50s protein, resulted, after selection, in plasmids being obtained which contain the insert in an antisense orientation (Ldi antisense), allowing the under-expression of the PSA in the modified *L. infantum* promastigotes.

Advantageously, it was found that these results could be generalized both as regards the *leishmania* species and as regards the gene inserts encoding antigenic proteins that can be used.

The aim of the invention is therefore to provide novel expression vector constructs for genes encoding antigenic *leishmania* promastigote proteins.

The invention is also directed toward the use of these constructs for obtaining avirulent *leishmania* promastigote mutants.

According to yet another aspect, the invention is directed toward the uses of these avirulent mutants for immunoprophylactic purposes.

The expression vectors according to the invention are characterized in that they contain an insert, in an antisense orientation, of a gene encoding an antigenic *leishmania* promastigote peptide or protein.

Advantageously, the cloning into expression vectors of said genes in an antisense orientation allows the peptide or the protein to be underexpressed in the modified *leishmania promastigotes*.

Preferably, said vectors are characterized in that they contain a *leishmania* PSA gene insert.

In one embodiment of the invention, it is an *L. amazonensis* gene insert.

The *L. amazonensis* PSA genes are more especially chosen from the group comprising SEQ ID Nos. 1 to 5.

In another preferred embodiment of the invention, it is an *L. infantum* gene insert.

The *L. infantum* genes are advantageously chosen from the group comprising SEQ ID No. 6.

The invention is also directed toward genetically modified *leishmania* promastigotes, characterized in that they are avirulent mutants, transfected with a vector as defined above.

The invention is also directed toward a method of obtaining avirulent forms of *leishmania promastigotes*, characterized in that it comprises:

nondirectional insertion, into an expression vector, of genes encoding antigenic *leishmania* peptides or proteins, selection of the constructs containing the inserts in an antisense orientation, transfection of *leishmania* promastigote forms using the selected constructs, biological cloning of the genetically transformed promastigotes by micromanipulation so as to obtain mutants which underexpress, or even which no longer express, the gene encoding an antigenic *leishmania* promastigote protein.

The transfection of the promastigote forms is advantageously carried out by electroporation.

Revelation of the peptide or of the protein by Western blotting makes it possible to estimate its level of production in the clones.

The use of the above arrangements makes it possible to study the consequences of the underexpression of antigenic *leishmania* peptides or proteins on the behavior of the transformed promastigotes and to thus identify their biological role.

To this effect, the various genetically modified parasites were cloned by micromanipulation (biological cloning) and characterized and compared at the molecular level (level of production of the antigenic protein, level of expression of the corresponding transcripts). The phenotypic characterization of the genetically modified and cloned promastigotes consisted in comparing the growth kinetics of these parasites and also their infectious capacity in vitro with respect to canine macrophages.

The characterization of a parasitic virulence factor, such as PSA, makes it possible to develop novel strategies for interference with the infectious process for therapeutic and/or vaccine-related purposes.

In particular, the invention makes it possible to obtain attenuated, or even avirulent, strains that can be used in animal and/or human vaccination.

Figure 2:
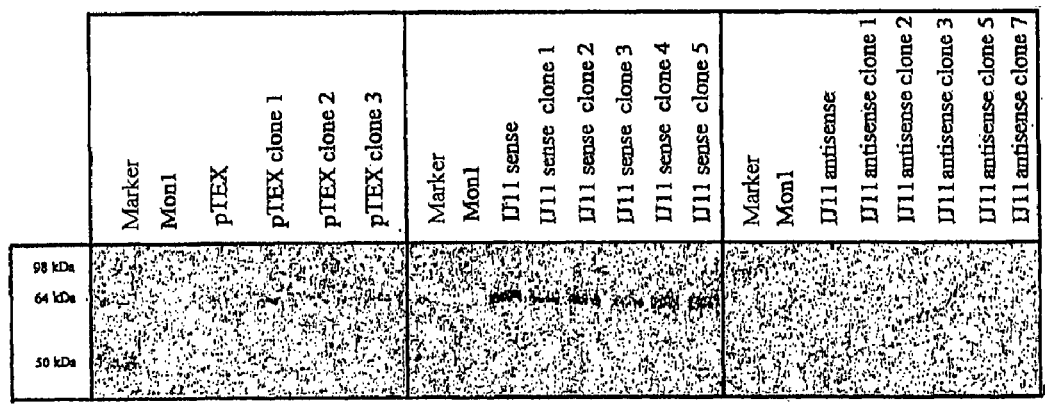
Figure 3:
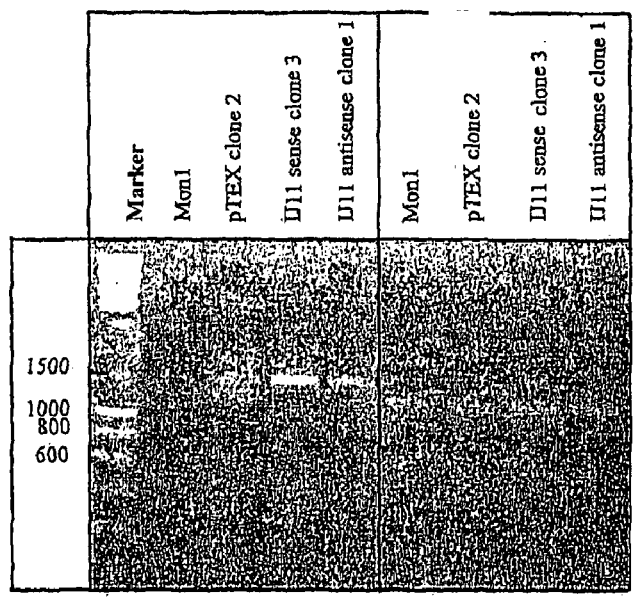
Figure 4:
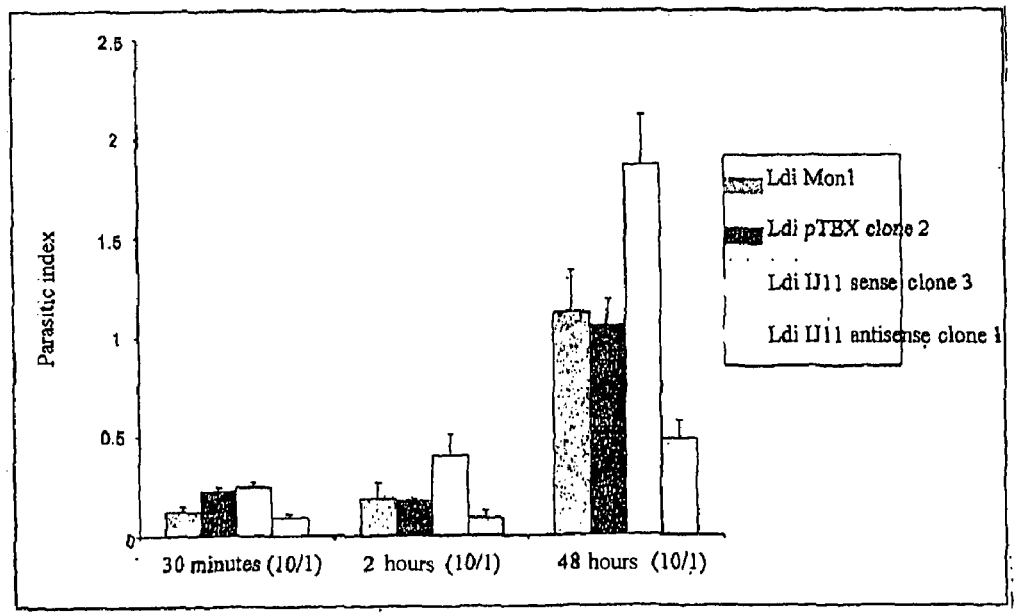

Other characteristics and advantages of the invention are given in the examples which follow with reference to FIGS. 1 to 4, which represent, respectively, FIGS. 1 and 2, the results of analysis by Western blotting of the PSA of total polypeptide extracts of a wild-type strain of Ldi Mon1 and of excretory/secretory antigens of culture supernatants of wild-type strains, of sense and anti-sense transformed parasitic parent strains and of clones thereof;

FIG. 3, results of RT-PCR on transcripts of a gene encoding PSA and of a housekeeping gene;

FIG. 4, the parasitic index determined over the course of the in vitro infection of canine macro-phages with a wild-type strain or clones.

MATERIALS AND METHODS

I—In Vitro Cultures
1—Axenic Cultures of *L. infantum*

The wild-type strain of *Leishmania infantum* used in the studies described hereinafter bears the WHO reference: MHOM/MA/67/ITMAP-263/clone2, zymodeme MON-1. The transformed strains were obtained after cloning of the IJ11 gene (1404 bp), encoding the *L. infantum* PSA (56 kDa), in the sense or antisense position in the expression vector pTEX, and then transfection by electroporation into the promastigote form of *L. infantum*. The Ldi IJ11 antisense, Ldi pTEX transformed parasites were selected in the presence of increasing concentrations of geneticin up to 50 µg/ml. The presence of the plasmid and the orientation of the transgene (antisense) were verified by Southern blotting and the level of transcription of the transgene was verified by Northern blotting.

The promastigote forms are cultured under axenic conditions in a completely defined culture medium containing no macromolecule as serum substitute (serum-free RPMI 199H medium, pH 7), but also in RPMI 1640 medium containing 20% of decomplemented fetal calf serum (20% serum RPMI medium, pH 7.2), and supplemented with penicillin (100 units/ml) and with streptomycin (100 µg/ml). The various transformed strains were cloned by the micromanipulation technique. A single parasite is sampled under a microscope using a fine glass needle and deposited on NNN medium (Novy, macNeal, Nicolle). The culturing of the parasites is carried out by successive subculturings in 20% RPMI medium. The genetically modified promastigote forms and the corresponding clones are maintained in continuous culture by weekly subculturings in serum-containing culture media or adapted in serum-free medium at 25° C. in the presence of geneticin (50 µg/ml). The parasite concentration is determined by flow cytometry (FacsCalibur, Beckton Dickinson). The parasites are conserved by cryofreezing of the organisms in culture in the presence of 3% DMSO (dimethyl sulfoxide) at −180° C. in liquid nitrogen.

2—Macrophage Cultures

PBMCs (Peripheral Blood Mononuclear Cells) are isolated from whole blood of a normal dog by Ficoll gradient (Ficoll Lymphoprep®, density 1.077±0.001 g/ml; AbCys, France) and by centrifugation at 700 g for 20 min at ambient temperature. The cells are then washed 3 times in PBS (0.01M phosphate buffered saline, pH 7.2) without $Ca^{2+}$/$Mg^{2+}$ by centrifugation at 400 g for 10 min at 4° C., before being resuspended in RPMI 1640 supplemented with 10% of fetal calf serum, 100 units/ml of penicillin and 100 µg/ml of streptomycin, and then cultured at 37° C.

II—Harvesting and Preparation of the Parasite Material

1—Harvesting of the Parasite Material

The promastigote forms in the stationary growth phase (7 days) are harvested by centrifugation of the serum-free parasite cultures at 3000 g for 10 min at 4° C. The parasite pellets and the culture supernatants thus dissociated are then treated separately.

2—Preparation of Parasite Lysates

The parasite pellet is washed twice in PBS under the centrifugation conditions described above. After the final wash, the number of parasites harvested is determined by flow cytometry. $10^9$ washed parasites are resuspended in a hypotonic lysis solution: 50 mM Tris, pH 8, containing 1% of Triton X100 (Sigma). After incubation at 4° C. for 20 min, centrifugation for 20 min at 4° C. and at 2000 g makes it possible to separate the insoluble material (debris) from the supernatant (soluble molecules). This supernatant corresponds to a total polypeptide extract (TPE).

3—Concentration of the Excretory/Secretory Antigens (ESAs) from the Culture Supernatant Metabolized by the Parasites 10 ml of supernatant metabolized by the parasites are filtered through a Millipore membrane (0.22 µm) and then frozen in shells before being freeze-dried. The freeze-dried materials are taken up in 1 ml of milliQ water in order to be dialyzed for 48 h at 4° C. so as to remove the salts. A second freeze-drying process makes it possible to concentrate the supernatant 200-fold.

III—Biochemical Analyses

1—Protein Assay

The assaying of the proteins is carried out using the Beckman DU-600 spectrophotometer, at 595 nm, according to the Bradford method, using the Biorad reagent (Biorad Protein Assay Kit 11). A standard range, from 5 to 20 µg/ml, is prepared from a standard bovine albumin solution (1 mg/ml BSA, Sigma).

2—SDS-PAGE (Sodium Dodecyl Sulfate-Polyacrylamide Gel Electrophoresis) Analysis

The SDS-PAGE polyacrylamide gel analysis was carried out in a mini-gel electrophoresis tank (Biorad). The acrylamide percentages used are 5% for the stacking gel and 10% for the separating gel, thereby making it possible to separate proteins of 10 to 200 kDa. TPE protein concentrations are mixed (v/v) with sample buffer containing 4% SDS, 20% glycerol and 0.5% bromo-phenol blue in 0.5M Tris-HCl, pH 6.8.

The electrophoretic migration is carried out in a buffer (2.5 mM Tris/19.2 mM glycine, pH 8.3) containing 0.1% SDS under a constant voltage of 80V. The calibration of the gel is obtained by depositing 10 µg of standard proteins of known molecular weights (Mark12 Wide Range Protein Standard/SeeBlue® Plus2 Pre-Stained Standard, Novex).

3—Revelation of the Proteins with Silver Nitrate

After removal of the SDS by washing in the presence of acetic acid (10%) and ethanol (40%) for 1 h, the acetic acid is then itself removed by two rinses for 30 min in 50% ethanol. The gels are then incubated for 15 min in a staining mixture: 19.4% $AgNO_3$-0.36% NaOH. After 5 washes in milliQ water, a revealing solution containing 0.02% formaldehyde in 1% citric acid (w/v) reveals the proteins on the gel. The revelation threshold for this staining method is 2 ng of protein equivalent.

IV—Immunoanalyses

1—Western Blotting

After having been separated in an SDS-PAGE polyacrylamide gel, the proteins are blotted onto a nitrocellulose membrane (Amersham, Hybond-C Extra). The blotting is carried out under semi-dry conditions. The membranes are then saturated for one hour in a TBS-5% milk blocking solution. The membranes are incubated overnight at ambient temperature and with agitation, with the F5 monoclonal antibody directed against PSA and obtained in mice (MAB F5), diluted to 1/50 in TBS. After 3 washes for 5 min in TBS, the bound antibodies are detected with peroxidase-coupled anti-mouse immunoglobulin G secondary antibodies (Tebu) diluted to 1/500 in TBS and incubated for 45 min at ambient temperature with agitation. Next, 3 washes for 5 min in TBS are carried out before revealing the reaction with a solution containing 15 mg of 4-chloro-1-naphthol dissolved in 5 ml of methanol, to which are added 25 ml of TBS containing 15 µl of 30% $H_2O_2$. The reaction is stopped by washing the membrane with distilled water.

2—Indirect Immunofluorescence on Parasites

The parasites in the stationary phase of their culture (7 days) are fixed with 1% formaldehyde in PBS without $Ca^{2+}$/$Mg^{2+}$, and then washed. Once fixed, the parasites are deposited on Teflon-coated wells (10 wells, 50 ml/well) and dried in the open air. Each well is then processed with the F5 monoclonal antibody (MAB F5) diluted in a (saturating) blocking solution (1% goat serum, 0.5% BSA in PBS) for 30 min at 37° C. The cells are then washed and incubated for 30 min at 37° C. with the second antibody conjugated to fluorescein isothiocyanate (FITC) (goat anti-mouse immunoglobulin G antiserum) diluted to 1/300 in a solution of PBS containing Evans blue at 1/7500. The slides are observed under a photon fluorescence microscope (Leitz).

V—Molecular Analysis

1—Total RNA Extraction

The promastigote forms are harvested by centrifugation of the serum-free parasite cultures at 3000 g for 10 min at 4° C. The parasite pellet is washed twice in PBS under the above centrifugation conditions. After the final wash, in order to lyse the parasites and to inhibit the endogenous ribonucleases (RNAses), the cells are dissociated by vortexing in 1 ml of Trizol (Trizol Reagent, GibcoBRL), and then incubated for 5 min at ambient temperature. The lysate is incubated in 0.2 ml of chloroform for 2 min at ambient temperature, and then centrifuged at 12,000 g for 15 min at 4° C. so as to give two phases, an aqueous phase and an organic phase. The RNAs are exclusively in the aqueous phase, which is recovered. The RNAs are then precipitated by adding 0.5 ml of isopropanol and incubated for 10 min at ambient temperature, and then centrifuged at 12,000 g for 10 min at 4° C. The pellet is washed in 1 ml of 75% ethanol, and then centrifuged at 7500 g for 5 min at 4° C., before being taken up in 40 µl of water (RNAse-free). In order to remove any possible presence of DNA, the dissolved RNA pellet is taken up in 1 µl of DNAse I+0.1 volume of 10×DNAse I buffer, and incubated for 20 min at 37° C. After the addition of 5 µl of DNAse inactivation reagent, incubation for 2 min at ambient temperature and then centrifugation at 10,000 g for 1 min at 4° C., the supernatant containing the RNAs is recovered. The total RNA is quantified by spectrophotometry, the absorbance being read at 260 nm (1 OD unit=40 µg/ml of single-stranded RNA). The quality of the extracted RNA and the amount and the size are verified by electrophoresis on 1% agarose gel in 0.5×TAE buffer, in the presence of 0.01% ethidium bromide (ETB). The size marker used is the SmartLadder (Eurogentec). The total RNA is then visualized under UV at 312 nm after migration. The selected criteria for quality of the extraction are the absence of DNA and the visualization of 3 ribosomal RNA bands of equal intensity.

2—RT-PCR

The single-stranded cDNA is synthesized by carrying out an RT-PCR with 1 µg of total RNA, 2 µl of dNTP mix (5 mM), 0.2 µl of specific primers (10 µM) and $H_2O$ qs 13 µl. The mix is incubated for 2 min at 65° C. and then for 2 min in ice, before the following are added: 4 µl of 5× buffer, 1 µl of DTT (0.1M), 1 µl of Superase In (40U) (RNAse Inhibitor, Ambion) and 1 µl of SuperScript™ (200U) (Reverse Transcriptase, Invitrogen). The mix is incubated for 50 min at 42° C., and the reaction is then inactivated by heat shock for 15 min at 70° C.

The single-stranded cDNA is amplified by PCR with 3 µl of cDNA, 12.5 µl of PCR Mastermix (Promega), 1 µl of 5'P and 3'P specific primers (10 µM) and $H_2O$ qs 25 µl.

The following primers were used:

```
SEQ ID No. 7  -nhinsp1: 5'-CATCGCTTACCCCTTGTT-3'
SEQ ID No. 8  -nhinsp2: 5'-GTGGCCAATCGCGACA-3'
SEQ ID No. 9  -P1RT:    5'-ATGGCGCTGTGCGTGCGTCGG-3'
SEQ ID No. 10 -P4RT:    5'-GCGCGCGACAGCAGCGGCAT-3'.
```

The program of the PCR reaction used and carried out in a thermocycler (GeneAmp PCR System 2400, Applied Biosystems) is the following: 5 min at 94° C., then 27 cycles (94° C. 30 sec, 55° C. 1 min, 72° C. 1 min) and 10 min at 72° C.

The PCR products are verified by 1% agarose gel electrophoresis.

VI—Biological Analysis

1—Growth Kinetics

The in vitro culture kinetics were realized over 10 days in RPMI 20% medium, starting from an initial concentration of $5 \times 10^5$ parasites/ml. The parasite concentration is determined by flow cytometry (FacsCalibur, Beckton Dickinson), by mixing 500 µl of PBS, 5 µl of culture and 0.5 µl of propidium iodide.

2—In Vitro Infection in Parasite/Macrophage Interactions $10^6$ PBMCs/well (200 µl), isolated from normal dog whole blood, are distributed in LabTek® culture chambers (Nalge Nunc International). After incubation for 30 min at 37° C., 5% $CO_2$, the LabTek® are washed gently with RPMI 10% in order to remove the cells which have not adhered. The macrophages are obtained from the cultured monocytes after 5 days of maturation. The mature macrophages are infected in vitro with promastigote forms in the stationary culture phase, for 30 min, 2 h and 48 h at 37° C. and 5% $CO_2$ at a parasite:macrophage ratio of 10:1. The macrophages are then washed gently twice in order to remove the nonphagocytozed parasites. After 30 min, 2 h and 48 h, the cells are fixed with methanol and stained with Giemsa. 300 macrophages are observed under an immersion optical microscope (1000× magnification), and the percentage of parasitized macrophages, the number of amastigotes per macrophage and the parasitic index (P.I.) are determined. The P.I. is equivalent to the percentage of infected macrophages multiplied by the number of amastigotes per macrophage.

Results

Evaluation of the Level of Production of PSA in the Transformed Clones

FIGS. 1 and 2 report the results of Western blotting analysis of the PSA, respectively, of total polypeptide extracts (TPE) derived from the parasite pellets of the wild-type strain Ldi Mon1, on excretory/secretory antigens (ESAs) derived from metabolized culture medium supernatants of the wild-type strain Ldi Mon1, of the parent strains of transformed parasites (Ldi pTEX, Ldi IJ11 sense and Ldi IJ11 antisense) and of their corresponding clones (5 µg protein equivalent of total extract per lane). It is noted that no band is observed for the wild-type strain Ldi Mon1, that the overexpression is, on the other hand, clearly visible for Ldi IJ11 sense, both at the level of the TPEs and the ESAs, compared with the expression in Ldi pTEX, and that a decrease in the expression of the PSA is observed with Ldi IJ11 antisense.

Analysis of the PSA Transcripts by RT-PCR

An RT-PCR was carried out on the transcripts of the gene encoding the PSA and also on the transcripts of a housekeeping gene encoding nucleoside hydrolase.

The results obtained are given in FIG. 3. A significant increase in the level of the transcripts encoding the PSA is observed in Ldi IJ11 sense, and a notable decrease is observed in Ldi IJ11 antisense, compared with Ldi pTEX. No signal is observed with the wild-type strain of Ldi Mon1.

In Vitro Infectious Capacity in the Parasite-Macrophage Interactions

FIG. 4 reports the parasitic index determined during the in vitro infection of canine macrophages with the wild-type strain or the various selected clones at various incubation times: 30 min (parasite attachment to the macrophages), 2 h (parasite penetration) and 48 h (survival and multiplication of amastigotes).

It is noted that, at 30 min and at 2 h, the Ldi IJ11 sense promastigotes exhibit a parasitic index which is approximately two times higher than those of Ldi IJ11 antisense is approximately two times lower. The same results are obtained after 48 h of infection.

VII—Study of the In Vivo Role of the pTEX, Sense and Antisense Mutant

Infection of Balb/C Mice by IP Injection with $10^8$ Promastigotes/100 µl

Protocol for Measuring Parasitemia (Parasite Burdens)

BIBLIOGRAPHIC REFERENCE

P. A. Buffet et al., 1995. *Antimicrobial agents and chemotherapy*. Vol. 39: 2167-2168

Prepare:
 1 tube of 15 ml per organ with 4 ml of SDM or RPMI medium/20% FCS
 Weigh the tubes+medium (weight=T in g)
 Cell Strainer+small Petri dishes (1 cell strainer for two same organs belonging to the same group/batch of mice)+1 ml syringe On spleen and liver organs:
For the spleen: remove the entire spleen
For the liver: remove only the small lobe
  Weighing of organs (organ in tube+medium, weight=TO in g)
  Grinding/homogenization with a Potter homogenizer or cell strainer in 4 ml of medium.
For parasitemia/spleen:
  In a 96-well plate, remove 250 µl of cells for the 1st well and prepare doubling dilutions with 150 µl of parasites in 150 µl of medium, and then, for the following wells, remove 150 µl to be diluted in 150 µl of medium, etc. Prepare 2×12 wells of dilutions (2 rows).
  After incubation for 7 and 15 days at 26-28° C., the plates are examined under an inverted microscope (×100 or ×200 objective).
  Note the absence or the presence of parasites for each well.
  Note the last well where parasites are present.
For parasitemia/liver:
  In a 96-well plate, remove 25 µl of cells for the 1st well containing 225 µl of medium and prepare 4-fold serial dilutions with 50 µl of parasites in 150 µl of medium, and then, for the following wells, remove 50 µl to be diluted in 150 µl of medium, etc. Prepare 2×12 wells of dilutions (2 rows).
  After incubation for 7 and 15 days at 26-28° C., the plates are examined under an inverted microscope (×100 or ×200 objective).
  Note the absence or the presence of parasites for each well.
  Note the last well where parasites are present.
  The final titer corresponds to the last dilution for which the well contains at least 1 parasite.
  The number of parasites per gram (parasite burden) in the corresponding organ is calculated in the following way:

Number of parasites=(geometric mean of the inverse titers of each duplicate/weight of section homogenized)×400

$$\text{Parasite burden} = \frac{\text{inverse of the limiting dilution}}{\text{organ weight (g)}} \times 400$$

N.B.:—400 corresponds to the inverse fraction of the homogenized organ inoculated in the 1st well
<10³ to >10⁶
Point at 14 days after infection:
Parasitemia (reading at 15 days) carried out in duplicate and doubling dilutions Parasite burden=(inverse of the limiting dilution/organ weight (g))×400

| | Organ weight (g) | Limiting dilution | Parasite burden Parasite g-1 | Mean Parasite burden | Standard deviation | General mean Parasite burden | Standard deviation g | |
|---|---|---|---|---|---|---|---|---|
| | | | | Batch 1 pTEX | | | | |
| Mouse 1 spleen | 0.14 | 0.0078 | 366300 | 274725 | 129507 | 107912 | 56756 | without mouse 1 trial |
| | 0.14 | 0.0156 | 183150 | 183150 | | | | |
| Mouse 2 spleen | 0.16 | 0.0156 | 160256 | 120064 | 56840 | | | without mouse 1 trial |
| | 0.16 | 0.0313 | 79872 | | | 67348 | 22927 | 1 and 2 and |
| Mouse 3 spleen | 0.14 | 0.0625 | 45714 | 68498 | 32222 | | | without mouse 2 trial |
| | 0.14 | 0.0313 | 91283 | | | | | |
| Mouse 4 spleen | 0.16 | 0.0625 | 40000 | 59936 | 28194 | | | |
| | 0.16 | 0.0313 | 79872 | | | | | |
| | | | | Batch 2 sense | | | | |
| Mouse 1 spleen | 0.14 | 0.5 | 5714 | 2857 | 4041 | 2367 | 1517 | |
| | 0.14 | nothing | 0 | | | | | |
| Mouse 2 spleen | 0.19 | nothing | 0 | 2105 | 2977 | | | |
| | 0.19 | 0.5 | 4211 | | | | | |
| Mouse 3 spleen | 0.24 | 1 | 1667 | 833 | 1179 | | | |
| | 0.24 | nothing | 0 | | | | | |
| Mouse 4 spleen | 0.17 | 0.25 | 9412 | 7059 | 3328 | | | |
| | 0.17 | 0.5 | 4706 | 4706 | | | | |
| Mouse 5 spleen | 0.15 | 1 | 2667 | 1333 | 1886 | | | |
| | 0.15 | nothing | 0 | | | | | |
| | | | | Batch 3 antisense | | | | |
| Mouse 1 spleen | 0.13 | 0.25 | 12308 | 12308 | 0 | 8744 | 2458 | |
| | 0.13 | 0.25 | 12308 | | | | | |
| Mouse 2 spleen | 0.14 | 1 | 2857 | 1429 | 2020 | | | |
| | 0.14 | nothing | 0 | | | | | |
| Mouse 3 spleen | 0.15 | 0.5 | 5333 | 8000 | 3771 | | | |
| | 0.15 | 0.25 | 10667 | | | | | |
| Mouse 4 spleen | 0.18 | 0.25 | 8889 | 6667 | 3143 | | | |
| | 0.18 | 0.5 | 4444 | | | | | |
| Mouse 5 spleen | 0.20 | 0.25 | 8000 | 8000 | 0 | | | |
| | 0.20 | 0.25 | 8000 | | | | | | results in red not taken into account

| Summary point 15 d | | | |
|---|---|---|---|
| | Mean Parasite burden | Standard deviation | Mean deviation |
| Batch 1 pTEX | | | |
| Mouse 1 spleen | 274725 | 129507 | 91575 |
| Mouse 2 spleen | 120064 | 56840 | 40192 |
| Mouse 3 spleen | 68498 | 32222 | 22784 |
| Mouse 4 spleen | 59936 | 28194 | 19936 |
| Batch 2 sense | | | |
| Mouse 1 spleen | 2857 | 4041 | 2857 |
| Mouse 2 spleen | 2105 | 2977 | 2105 |
| Mouse 3 spleen | 833 | 1179 | 833 |
| Mouse 4 spleen | 7059 | 3328 | 2353 |
| Mouse 5 spleen | 1333 | 1886 | 1333 |
| Batch 3 antisense | | | |
| Mouse 1 spleen | 12308 | 0 | 0 |
| Mouse 2 spleen | 1429 | 2020 | 1429 |
| Mouse 3 spleen | 8000 | 3771 | 2667 |
| Mouse 4 spleen | 6667 | 3143 | 2222 |
| Mouse 5 spleen | 8000 | 0 | 0 |

| Summary point 15 d | | |
|---|---|---|
| | Mean Parasite burden | Standard deviation |
| pTEX mouse 2 spleen | 120064 | 56840 |
| pTEX mouse 3 spleen | 68498 | 32222 |
| pTEX mouse 4 spleen | 59936 | 28194 |
| Sense mouse 1 spleen | 2857 | 4041 |
| Sense mouse 2 spleen | 2105 | 2977 |
| Sense mouse 3 spleen | 833 | 1179 |
| Sense mouse 4 spleen | 7059 | 3328 |
| Sense mouse 5 spleen | 1333 | 1886 |
| Antisense mouse 1 spleen | 12308 | 0 |
| Antisense mouse 2 spleen | 1429 | 2020 |
| Antisense mouse 3 spleen | 8000 | 3771 |
| Antisense mouse 4 spleen | 6667 | 3143 |
| Antisense mouse 5 spleen | 8000 | 0 |
| | Parasite burden | Standard deviation |
| pTEX | 82833 | 3252 |
| Sense | 2838 | 248 |
| Antisense | 7281 | 390 |

| Parasitemia (2 months) | | | | | | |
|---|---|---|---|---|---|---|
| SPLEEN | Organ weight (g) | Limiting dilution | Parasite burden parasite g-1 | Mean Parasite burden | General mean Parasite burden | Standard deviation g |
| Batch 1 pTEX | | | | | | |
| Mouse 1 spleen | 0.14 | 0.016 | 182857 | | 264127 | 118470 |
| Mouse 2 spleen | 0.14 | 0.008 | 365714 | | | |
| Mouse 3 spleen | 0.17 | 0.031 | 75294 | | | |
| Mouse 4 spleen | 0.18 | 0.016 | 142222 | | | |
| Mouse 5 spleen | 0.14 | 0.008 | 365714 | | | |
| Batch 2 sense | | | | | | |
| Mouse 1 spleen | 0.1 | NI | 0 | | 0 | 0 |
| Mouse 2 spleen | 0.15 | NI | 0 | | | |
| Mouse 3 spleen | 0.12 | NI | 0 | | | |
| Mouse 4 spleen | 0.14 | NI | 0 | | | |
| Mouse 5 spleen | 0.14 | NI | 0 | | | |
| Batch 3 antisense | | | | | | |
| Mouse 1 spleen | 0.11 NI | | 0 | | 1813 | 2914 |
| Mouse 2 spleen | 0.12 | 0.500 | 6667 | | | |
| Mouse 3 spleen | 0.19 | 0.500 | 4211 | | | |
| Mouse 4 spleen | 0.13 NI | | 0 | | | |
| Mouse 5 spleen | 0.14 NI | | 0 | | | |
| Mouse 6 spleen | 0.18 NI | | 0 | | | |

| | Parasite burden g-1 | | Standard deviation | |
|---|---|---|---|---|
| Spleen | 15 days | 2 months | 15 days | 2 months |
| pTEX | 107912 | 264127 | 56756 | 118470 |
| Sense | 2367 | 0 | 1517 | 0 |
| Antisense | 8744 | 1813 | 2458 | 2914 |
| pTEX | 67348 | 264127 | 22927 | 118470 |
| Sense | 2367 | 0 | 1517 | 0 |
| Antisense | 8744 | 1813 | 2458 | 2914 | results in red not taken into account
NI = non infected

| LIVER | Organ weight (g) | Limiting dilution | Parasite burden parasite g-1 | Parasitemia (2 months) | | |
|---|---|---|---|---|---|---|
| Batch 1 pTEX | | | | 2495238 | 4025557 | with mouse 1 |
| Mouse 1 liver | 0.12 | 0.000391 | 8533333 | | | |
| Mouse 2 liver | 0.1 | 0.000024 | 163840000 | 482540 | 43989 | without mouse 1 |
| Mouse 3 liver | 0.14 | 0.006250 | 457143 | | | |
| Mouse 4 liver | 0.14 | 0.006250 | 457143 | | | |
| Mouse 5 liver | 0.12 | 0.006250 | 533333 | | | |
| Batch 2 sense | | | | | | |
| Mouse 1 liver | 0.17 | NI | 0 | 0 | 0 | 0 |
| Mouse 2 liver | 0.18 | NI | 0 | | | |
| Mouse 3 liver | 0.12 | NI | 0 | | | |
| Mouse 4 liver | 0.14? | NI | 0 | | | |
| Mouse 5 liver | 0.09 | NI | 0 | | | |
| Batch 3 antisense | | | | | | |
| Mouse 1 liver | 0.12 | NI | 0 | | 38889 | 61162 |
| Mouse 2 liver | 0.16 | 0.025 | 100000 | | | |
| Mouse 3 liver | 0.1 | NI | 0 | | | |
| Mouse 4 liver | 0.08 | NI | 0 | | | |
| Mouse 5 liver | 0.12 | 0.025 | 133333 | | | |
| Mouse 6 liver | 0.1 | NI | 0 | | | |

What is claimed is:

1. An expression vector for a gene encoding an antigenic *leishmania* promastigote protein, characterized in that it comprises an insert of an excreted/secreted Promastigote Surface Antigen (PSA) gene in an antisense orientation, wherein said PSA is not gp63.

2. The vector as claimed in claim 1, characterized in that it contains an *L. amazonensis* gene insert.

3. The vector as claimed in claim 2, characterized in that the *L. amazonensis* gene comprises one of SEQ ID NOs: 1 to 5.

4. The vector as claimed in claim 1, characterized in that it contains an *L. infantum* gene insert.

5. The vector as claimed in claim 4, wherein the vector comprises the nucleotide sequence set forth in SEQ ID NO:6.

6. A genetically modified *leishmania* promastigote, characterized in that it is an avirulent mutant, transfected with a vector as claimed in claim 1.

* * *

SEQUENCE LISTING

<160> NUMBER OF SEQ ID NOS: 10

<210> SEQ ID NO 1
<211> LENGTH: 2333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1 gaccctgtt   gcgaatggcg   cagtgcgtgc   gtcggctggt   gctggcggcg   cccctcgccg    60
ctgtggtggc   gctgctgctg   tgcacgagca   gtgcaccggt   ggcgcgtgct   gcgggacga   120 gcgacttcac   tgaggcgcag   cagacgaaca   cgctgacggt   gctgcaggcg   tttgcgcgtg   180
cgatccctgc   gcttggggac   acgtggacgg   gcagcgactt   ctgctcgtgg   aagcacatca   240
tctgcgactc   ccccggcgtc   ggcgtgtgga   tgggcgatgt   ggattatacc   ggcacgctgc   300
cggagatgcc   tgcgagcgtc   gactacaagg   acgtcatgat   cacggaactg   aacttcagcg   360
caatgggcca   ggggctgagc   gggacgctgc   cccctcatg    gagctcgctg   acgtccttga   420
tatcactgtg   catcgaaaag   tctgagaagg   tcaccggcac   gctgcctgcc   cagtggagct   480
cgatgacgtc   gctggacaac   cttaacctgc   acgacacggc   ggtctccggc   acgctgcctg   540
cccagtggag   ctcgatgaag   cagctgaccg   ttctggatct   ggagggcact   aaggtgtccg   600
gcacgctgcc   gtccgagtgg   agtgggatgg   cgaaggccga   ggccgtgcag   ctggagaact   660
gcggtctgtc   cgggagtctg   ccccctctgt   ggtctgcgat   gccgaagctg   cgtatcgtct   720
cactgagcgg   caaccacttc   tgcgggtgcg   tgcccgactc   gtggagggag   aaggaccgcc   780
tcgatgtgac   catcgaggaa   tggcacatgg   gcgaggactg   caagcttgct   aacgcctgcc   840
gcccgactgc   tgctccggga   acgaccacga   ctaacccgcc   caccaccacc   ggcaccccag   900
cagcctcctc   tactccttct   ccagggtcgg   ggtgcgaggt   ggatgggtgt   gaggtgtgcg   960

| | |
|---|---|
| aggggggactc cgctgcgcgg tgcgccaggt gccgtgaggg ctactccctg acggacgaga | 1020 |
| agacgtgcct ggcgaaccac gatggcgcg tggcggcggc gtcgagcgga gcggtggctg | 1080 |
| ccgctgctgt gtgggcggct gtgctgttga gcgtggggct ggtggcgtga gggtgcggcg | 1140 |
| ggcccctctt ctctgtggtg ccctggtgc ctgcctcgc cccggcacg gcgtcgtcgc | 1200 |
| tgccctctct cacccccacc agccgacggg gagaccgaca gccacacgcg cacgcgcaca | 1260 |
| cgccgtcgtg catcgcgtgt gctttccgcc gttgtggcgc ctgcacggat gcacgggcat | 1320 |
| gcggaggcgt gcatgcgtgt gcgcgtgcca gctcttgtgt gtctctccgt gtggccagca | 1380 |
| gtcggcaccc gcgccgatcg aatgcgcg cggcggcggt gtgtcgcctt ggacagcgga | 1440 |
| tgcgggcgcc cgcccctcgc cgtgtgccct gcggtctgct gtgctgccgc gcgagcgacg | 1500 |
| tacggatgcg ctgtccggcc ctcttcgacg gggctcgctt gcggtgctgt gctctcgtgg | 1560 |
| tctgtgccgg tgctgccctg gcggggtgag agctggcggg ggcgtgggtg cgcgcgcggc | 1620 |
| agctctccgc tgcgttgagg gcggcctgcc cctgcgtccg cgcaccgtcg cgctctcctc | 1680 |
| gacgccactg cgcgcgcttg ttggcttgct ttgctctgtc gtgcgcactc tctcttattt | 1740 |
| tccgtttcat tcgcctgtat tctcttctcc caccgcactg cggcctcgtc accgcggccg | 1800 |
| tgcggtgcgc aggcgggtga tgtgccgttg tgcccccct ttcatggcgc gctgggccga | 1860 |
| tcgccctctt gcctccctcc tccccctccc cctcccgccg gtcctgtcaa ttgtatatcc | 1920 |
| gtggacctta tcttcgtact gcctccgcgc ctcttccgta aagcttcgtt ggcgtgtgcc | 1980 |
| gcccccgga cgtcagcgcc gctgtgctcg catgctcacg gtgcgtcccc gtgcgtgggc | 2040 |
| gtgcacgtaa ggacatgtat atatgtatgt gtatgtatat gagtatgtat atatgtacgg | 2100 |
| ttatatatag gaatttgtgt atgttgaggt gtatgcatgt gcgtgcgtat attagtgtgt | 2160 |
| gcgagcacgc gtgttgcgcc acgctctgct gcccgcctcc gctgtgcgtg tcactcgctg | 2220 |
| tgggcgcggt ggcgggtggc gccgggtggt ggccgtgcgg cgggcggggg ctcctctgtg | 2280 |
| tttctctatt tctctgttcc ctgttgacct caaaaaaaaa aaaaaaaaaa aaa | 2333 |

<210> SEQ ID NO 2
<211> LENGTH: 1081
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2

| | |
|---|---|
| cgtggacggg cagcgacttc tgctcgtgga agcacatcat ctgcgactcc cccggcgtcg | 60 |
| gcgtgtggat gggcgatgtg gattataccg gcacgctgcc ggagatgcct gcgagcgtcg | 120 |
| actacaagga cgtcatgatc acggaactga acttcagcgc aatgggccag gggctgagcg | 180 |
| ggacgctgcc cccctcatgg agctcgctga cgtccttgat atcactgtgc atcgaaaagt | 240 |
| ctgagaaggt caccggcacg ctgcctgccc agtggagctc gatgacgtcg ctggacaacc | 300 |
| ttaacctgca cgacacggcg gtctccggca cgctgcctgc ccagtggagc tcgatgaagc | 360 |
| agctgaccgt tctggatctg gagggcacta aggtgtccgg cacgctgccg tccgagtgga | 420 |
| gtgggatggc gaaggccgag gccgtgcagc tggagaactg cggtctgtcc gggagtctgc | 480 |
| cccctcgtg gtctgcgatg ccgaagctgc gtatcgtctc actgagcggc aaccacttct | 540 |
| gcgggtgcgt gcccgactcg tggagggaga aggaccgcct cgatgtgacc atcgaggaat | 600 |
| ggcacatggg cgaggactgc aagcttgcta acgcctgccg cccgactgct gctcggaa | 660 |
| cgaccacgac taacccgccc accaccaccg gcaccccagc agcctcctct actccttctc | 720 |

```
cagggtcggg gtgcgaggtg gatgggtgtg aggtgtgcga gggggactcc gctgcgcggt      780
gcgccaggtg ccgtgagggc tactccctga cggacgagaa gacgtgcgtg gcgaaccacg      840
atggcggcgt ggcggcggcg tcgagcgag  cggtggctgc cgctgctgtg tgggcggctg      900
tgctgttgag cgtggggctg gtggcgtgag ggtgcggcgg gccctcttc  tctgtggtgc      960 ccctggtgcc tgccctcgcc cccggcacgg cgtcgtcgct gccctctctc accccacca      1020 gccgacgggg agaccgacag ccacacgcgc acgcgcacac gccgtcgtgc atcgcgtgtg      1080
c                                                                     1081
```

<210> SEQ ID NO 3
<211> LENGTH: 1371
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3

```
ggacgggcag cgacttctgc tcgtggaagc acatcatctg cgactccccc ggcgtcggcg       60
tgtggatggg cgatgtggat tataccggca cgctgccgga gatgcctgcg agcgtcgact      120
acaaggacgt catgatcatg gcactggact tcggcgcaat gggccaggga ctgagcggga      180
cgctgccccc ctcatggagc tcgctgacgt ccttgatgtc actgtggatc gaaaagtctg      240
agaaggtcac cggcacgctg cctacccagt ggagctcgat gaagcagctg acccttctgc      300
atctgaaggg cactaaggtg tccggcacgc tgccgcccga gtggagtggg atgacgtcgc      360
tggacgacct taacctgcac gacacggcgg tctccggcac gctgcctgcc cagtggagct      420
cgatgaagca gctgatcgat ctggatctgg agggcactaa ggtgtccggc acgctgccgc      480
ccgagtggag tgggatggcg aaggccgagg ccctgcagct gaagtactgc gatctgtccg      540
ggagtctgcc ccctcgtgg  tcttcgatgc agaagctgcg tatcgtctca ctgagcggca      600
accacttctg cgggtgcgtg cccgactcgt ggagggagaa ggaccgcctc gatgtgacca      660
tcgaggaatg gcacatgggc gaggactgca agcttgctaa cgcctgccgc ccgactgctg      720
ctccgggaac gaccacgact aacccgccca ccaccaccgg cacccc agca gcctcctcta      780 ctccttctcc agggtcgggg tgcgaggtgg atgggtgtga ggtgtgcgag ggggactccg      840
ctgcgcggtg cgccaggtgc cgtgagggct actccctgac ggacgagaag acgtgcctgg      900
cgaaccacga tggcggcgtg gcggcggcgt cgagcggagc ggtggctgcg gctgctgtgt      960
gggcggctgt gctgttgagc gtggggctgg tggcgtgagg gtgcggcggc ccctcttct   1020 ctgtggtgcc cctggtgcct gccctcgccc cagcacggc  gtcgtcgctg ccctctcacc     1080
cccaccagcc gaagggagag ccgacagcca cacgcacacg cgcacgcgcc gtcgtgcatc     1140
gcgtgtgctt tccgccgttg tggcgcctgc gcggatgcac gggcatgcgg aggcgtgcat     1200
gcgtgtgcgc gtgccagctc ttgtgtgtct ctccgtgtgg ccagcagtcg gcaccgcgc     1260 cgatcgaatg tgcgcgcggc ggcggtgtgt gccttggac  agcggatgcg gcgcccgccc     1320
ctcgccgtgt gccctgcggt ctgctgtgct gccgcgcgag cgacgtacgg a             1371
```

<210> SEQ ID NO 4
<211> LENGTH: 1203
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4

```
tcggcgtgtg gatgggcgat gtggattata ccggcacgct gccggagatg cctgcgagcg      60
tcgactacaa ggacgtcatg atcacggaac tgaacttcgg cgcaatgggc cagggactga     120
gcgggacgct gccccctca tggagctcga tgaagcagct gatcgatctg gatctggagg     180
gcactaaggt gtccggcacg ctgccgcccg agtggagtgg gatggcgaag gccgaggccc     240
tgcagctgaa gtactgcgat ctgtccggga gtctgccccc ctcgtggtct tcgatgcaga     300
agctgcgtat cgtctcactg agcggcaacc acttctgcgg gtgcgtgccc gactcgtgga     360
gggagaagga ccgcctcgat gtgaccatcg aggaatggca catgggcgag gactgcaagc     420
ttgctaacgc ctgccgcccg actgctgctc cgggaacgac cacgactaac ccgcccacca     480
ccaccggcac cccagcagcc tcctctactc cttctccagg gtcggggtgc gaggtggatg     540
ggtgtgaggt gtgcgagggg gactccgctg cgcggtgcgc caggtgccgt gagggctact     600
ccctgacgga cgagaagacg tgcctggcga accacgatgg cggcgtggcg gcggcgtcaa     660
gcggagcggt ggctgcggct gctgtgtggg cggctgtgct gttgagcgtg gggctggtgg     720
cgtgagggtg cggcgggccc ctcttctctg tggtgcccct ggtgcctgcc ctcgcccccg     780
gcacggcgtc gtcgctgccc tctctcaccc ccaccagccg acggggagac cgacagccac     840
acgcgcacgc gcacacgccg tcgtgcatcg cgtgtgcttt ccgccgttgt ggcgcctgca     900
cggatgcacg ggcatgcgga ggcgtgcatg cgtgtgcgcg tgccagctct tgtgtgtctc     960
tccgtgtggc cagcagtcgg cacccgcgcc gatcgaatgt gcgcgcggcg gcggtgtgtc    1020
gccttggaca gcggatgctg gcgcccgccc ctcgcgtgtg cctcggtctg cgtgtcgtgg    1080
ccgcgcgagc gacgtacgga gtgcgctgtc gccgggtggt ggccgtgcgg cgggcggggg    1140
ctcctctgtg tttctctatt tctctgttcc ctgttgacct caaaaaaaaa aaaaaaaaa     1200
aaa                                                                  1203
```

<210> SEQ ID NO 5
<211> LENGTH: 1207
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 5

```
ccggcgtcgg cgtgtggatg ggcgatgtgg attataccgg cacgctgccg gagatgcctg      60
cgagcgtcga ctacaaggac gtcatgatca cggaactgaa cttcagcgca atgggccagg     120
ggctgagcgg gacgctgccc cctcatggag ctcgctgac gtccttgata tcactgtgca     180
tcgaaaagtc tgagaaggtc accggcacgc tgcctgccca gtggagctcg atgacgtcgc     240
tggacaacct taacctgcac gacacggcgg tctccggcac gctgccgccc gagtggagtg     300
ggatgacgtc gctggacgac cttaacctgc acgacacggc ggtctccggc acgctgcctg     360
cccagtggag ctcgatgaag cagctgatcg atctggatct ggaggcact aaggtgtccg     420
gcacgctgcc gcccgagtgg agtgggatgg cgaaggccga ggccctgcag ctgaagtact     480
gcgatctgtc cggagtctg ccccctcgt ggtcttcgat gcagaagctg cgtatcgtct     540
cactgagcgg caaccacttc tgcgggtgcg tgcccgactc gtggagggag aaggaccgcc     600
tcgatgtgac catcgaggaa tggcacatgg gcgaggactg caagcttgct aacgcctgcc     660
gcccgactgc tgctccggga acgaccacga ctaacccgcc caccaccacc ggcaccccag     720
```

-continued

| | |
|---|---|
| cagcctcctc tactccttct ccagggtcgg ggtgcgaggt ggatgggtgt gaggtgtgcg | 780 |
| agggggactc cgctgcgcgg tgcgccaggt gccgtgaggg ctactcctga cggacgagaa | 840 |
| gacgtgcctg gcgaaccacg atggcggcgt ggcggcggcg tcaagcggag cggtggctgc | 900 |
| ggctgctgtg tgggcggctg tgctgttgag cgtggggctg gtggcgtgag ggtgccgccg | 960 |
| cccctcttc tctgtggtgc ccctggtgcc tgccctcgcc cccagcacgg ggtcgtcgct | 1020 |
| gccctctcac ccccaccagc cgaagggggag accgacagcc acacgcacac gcgcacgcgc | 1080 |
| cgtcgtgcat cgcgtgtgct ttccgccgtt gtggcgcctg cgcggatgca cgggcatgcg | 1140 |
| gaggcgtgca tgcgtgtgcg cgtgccaact cttgtgtgtc tctccgtgtg gccagcagtc | 1200 |
| ggcaccc | 1207 |

<210> SEQ ID NO 6
<211> LENGTH: 3088
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6

| | |
|---|---|
| gcgctgctgc cgctggcgct gttgtgtgtg tgctggggcc gcgccacgca cacgcacggt | 60 |
| agtgaggggg agccgcagcg accgaccggg cggagcgggc gggcggaggg gggcgctccc | 120 |
| gcccgctggt catgctctct gtttcgctgg ccggcctctc tacgccgctg cgtgggcgg | 180 |
| agctccgcgc tgcgtatcgc tcgccccctcg ctgcccctcc ctgcccctcc tcatgtgcac | 240 |
| tgctccctcc ctctccctcc ctctacactc ctcgctgtcc cctcggccga cctccacgga | 300 |
| cacgcagacg tgccgtgcgca tacacaccac ccctcacctc gctgctgctg ctgtgacagc | 360 |
| tctacggacc ctgcccagtc gctgcgcccc cgccacccgc ctctgtcccc cgcacgaggg | 420 |
| tacctacgac gtgccggcca ccccgctctg cccgataagc tgagctggcg ctcacgcccg | 480 |
| agcaatcccc tcacggatct gctgccgcgc cgcactgctc ttgaccctgg ctgcgaatgg | 540 |
| cgctgtgcgt gcgtcggctg gtgctggcgg cgaccctcgc cgctgtggtg gcgctgctgc | 600 |
| tgtgcacgag cagtgcgccg gtggcgcgtg ctgctgtgaa ggatgacttc actgctgcgc | 660 |
| agcggacgaa cacgctggcg gtgctggagg cgtttgggcg tgcgatccct gagcttggga | 720 |
| agctgtggaa gggcgacgac ttctgctttt gggagtcggt cgtgtgcgat gtgaccgaag | 780 |
| tgtacttgtg ggaaatcggt gcgacgtata ccggcacgct gccggagatg cctgtggacg | 840 |
| tcgactacac ggccgtcatg gtcaagcacc tcgactttc ccaaatgggg ctggggctga | 900 |
| gcggaacgct gccggacagc tggagcaggc tgcagggact gacctcactt acgttgtcgg | 960 |
| gctgcggcgt gagcggtacg ctgccccccct cgtggcgctc gatgaagtct ttggtgtcgt | 1020 |
| tgtggattga gagttgtgaa agtgttaccg gcaagctgcc gcctgagtgg agctcgatga | 1080 |
| aatcgctgag agatctccat ctgcatggcg cgaaggtttc cggcacgctg ccgcctgagt | 1140 |
| ggagcacgat gaaatcgctg acccttctcg atctgcagga cactcaggtt accggcagtc | 1200 |
| tgccgcctga gtgagctca atgaaatcca tgaccattct cagtctgaat ggcgcgaagg | 1260 |
| tttccggcac gctgccaccc cagtggagct cgatgacatc gctgagcctt ctcagtctgg | 1320 |
| agggtactca gctctccggc acgctaccgc cccagtggag tgggatgaca tcgctggtca | 1380 |
| cgcttttttct gcagggtact caggtctccg gcactctgcc gccgcagtgg agatcgatgt | 1440 |
| tgaatgccga gttcctgcag ctggagaact gcgacctgtc cggctgtttg ccccccgagt | 1500 |
| gggctgcgat gccgaagctg cgtcatgtcg aacttaaggg caaccagttc gccgggtgtg | 1560 |

```
tgccggactc gtgggctcag aaggccggtc tcgttgtgga aatcgaggat aagcacacgg    1620
gcaacagctg cattgctggt gcggactgcg caacgacgac cacgaccacc actgaaccca    1680
cgtccactgc gagcccaaca gccacgccta cctctgcccc cgagacgagg tgcgaggtgg    1740
atgggtgtga ggtgtgcgat ggggactccg cggcgaggtg cgccaggtgc cgtgagggct    1800
acttcctgac ggacgagagg acgtgcctgg tgtaccgcga tggcggcgtt gtggccgtgt    1860
cgatcggagc ggctgctgcc gctgttgtgt gcatggctgt gctgctgagc gtggggctgg    1920
cggcgtgagg atgccgctgc tgtcgcgcgc aggcggcggc acccgctgcg tggcacacga    1980
ctgcgtgctt gcgtgcagca ccgcgccctg cattggcgtg cgtgtgcgcg tctgtgtgtg    2040
catggctgct gacggtgcct ttcgtcctgc ctctcgctgc ctctgcctct ctccgcgtgt    2100
gaatgctgtg ggctgtgttt ggggctctcg tgcggcgctg ctgtacggct gctgcttctt    2160
ctccaccctc ctctctcgca tgccggcgag ggaggggtgg cacgtgcgcg tgtgccgctg    2220
cgcttgcgag tgcgtctgtg tgtgggcctt caccacgtgc tacggtcacg ccttctcggc    2280
tggccactcg cggcgctgag ggcggtgtgc ccttcccctc gagcgccgtc gcactctctt    2340
ccgcgcgcct gcgcgggctt cttcgtgcgc tgtgctcagc cgtgcgctct cacctctttc    2400 cctttcatt cgcttgtctt ctctcttctc cccccgcact gcggtctccc ctcctctgcc    2460
gtgcggtgcg caggcgggtg acttgccgtt gcgtctcccc ctttcgtgga gcgctgagcc    2520 gatcccctt cggcctccct cctccctcct cccgtgggtc ctgtctgttg tacatcgtcg    2580
gaccgtctct tcgtgttgcc tctccgcacc ttccgcaaat ctgcgctcgc ctgtgccgcc    2640
tctcggactt tatccttact gtgattgtat tctcacggtg cgtctccgtg tgtgtgtgtg    2700
ccacgcaccg cttcttccat gtgtgtcctt gcttgctctc gtctgccccc ccccctctgc    2760
ctcacacatt ccgtgcgtgt gtgcatcacc gttgggcggc gacatcggtg cccgtccctg    2820
ccaccctcta ctccctcatt ctcttgccac ttcgtgggcg gtgcgtgcat gcatggatgt    2880
atatacacgc atagaggggt ggggacgcgg gggatcctct agagtcgacc tgcaggcatg    2940
caagcttggc gtaatcatgg tcatagctgt ttcctgtgtg aaattgttat ccgctcacaa    3000
ttccacacaa catacgagcc ggaagcataa agtgtaaagc ctggggtgcc taatgagtga    3060
gctaactcac attaattgcg ttgcgctc                                      3088
```

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
catcgcttac cccttgtt                                                 18

<210> SEQ ID NO 8
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gtggccaatc gcgaca                                                   16

-continued

```
<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
atggcgctgt gcgtgcgtcg g                                            21

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gcgcgcgaca gcagcggcat                                              20
```